United States Patent [19]
Sato

[11] Patent Number: 5,998,626
[45] Date of Patent: Dec. 7, 1999

[54] BISBENZAZOLE COMPOUNDS

[75] Inventor: Tadahisa Sato, Kanagawa, Japan

[73] Assignee: Fuji Photo Film Co., Ltd., Kanagawa, Japan

[21] Appl. No.: 09/238,779

[22] Filed: Jan. 27, 1999

[30] Foreign Application Priority Data

Mar. 30, 1998 [JP] Japan .................................. 10-084757

[51] Int. Cl.[6] ...................... C07D 403/10; C07D 413/10; C07D 417/10
[52] U.S. Cl. .......................... 548/219; 548/156; 548/218; 548/305.4; 548/310.7
[58] Field of Search ................................... 548/156, 218, 548/219, 310.7, 305.4

[56] References Cited

U.S. PATENT DOCUMENTS 3,314,894  4/1967  Nyilas et al. ......................... 252/301.2

FOREIGN PATENT DOCUMENTS 59-194393  11/1984  Japan .............................. H05B 33/14
63-204692   8/1988  Japan .............................. H05K  1/11

*Primary Examiner*—Laura L. Stockton
*Attorney, Agent, or Firm*—Sughrue, Mion, Zinn, Macpeak & Seas, PLLC

[57] ABSTRACT

Disclosed are bisbenzazole compounds capable of emitting strong fluorescence, with the compounds having at particular positions specific substituent groups, such as alkoxy, aryloxy, dialkylamino, diarylamino or N-arylamino groups, to ensure high stability in organic photoluminescence elements. For example, bisbenzazole compounds show below are disclosed.

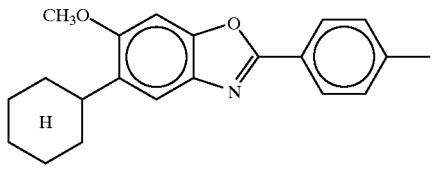

-continued

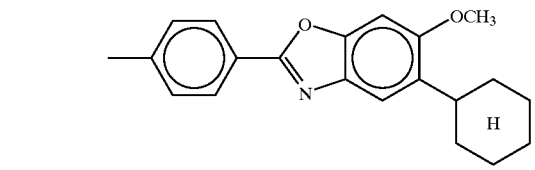

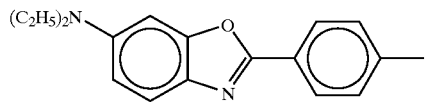

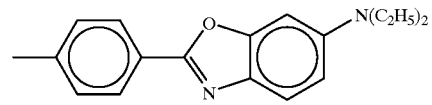

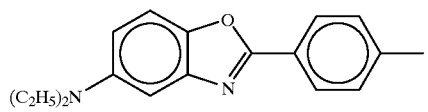

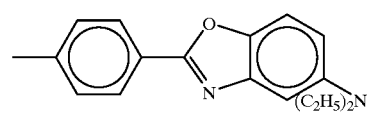

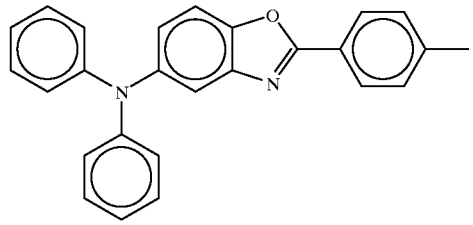

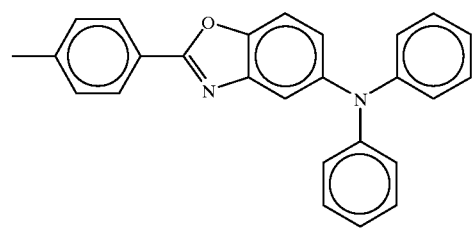

13 Claims, No Drawings

BISBENZAZOLE COMPOUNDS

FIELD OF THE INVENTION

The present invention relates to bisbenzazole compounds and, more particularly, to novel bisbenzazole compounds useful for an organic electroluminescence (EL) material and the like.

BACKGROUND OF THE INVENTION

It is disclosed by Tang et al. in JP-A-59-194393 and JP-A-63-264692 that compounds having a benzazole skeleton are of usefulness as an electron transfer compound and a luminous compound in the electron injection and transport zone of an internal junction organic electroluminescence element, or they are useful for a host material doped with a luminous substance. The term "JP-A" as used herein means an "unexamined published Japanese patent application". While the benztriazole skeleton-containing compounds as disclosed in those patents are desirable from the viewpoint of emitting strong fluorescence, they are insufficient in stability of vacuum deposition film and electron transferability. Accordingly, the stability of elements utilizing such compounds is far from being practical.

SUMMARY OF THE INVENTION

Thus, the present inventor has made a study for the purpose of finding what molecular structures enable the benzazole skeleton-containing compounds distinguished by emission of strong fluorescence to ensure enhanced stability in the elements utilizing them.

As a result, it has been found that the aforementioned purpose can be attained when bisbenzazole compounds have such a molecular structure that certain substituent groups are introduced thereinto. The present invention has been made on the basis of the information obtained by this study.

An object of the present invention is attained with novel bisbenzazole compounds represented by the following formulae (I) and (II) respectively:

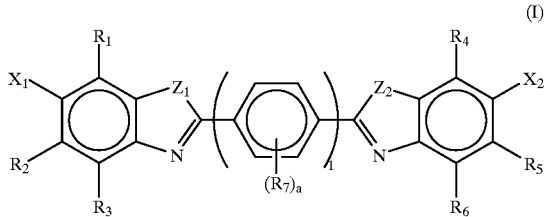

wherein each of the substituents $R_1$ to $R_7$ represents a hydrogen atom, a halogen atom, an alkyl group, an aryl group, an alkoxy group, an aryloxy group, an amino group, a dialkylamino group, an N-alkyl-N-arylamino group, a diarylamino group or a silyl group; l represents an integer of 1 or above; a represents an integer of from 1 to 4; $X_1$ and $X_2$ each represents an alkoxy group, an aryloxy group, a dialkylamino group, an N-alkyl-N-arylamino group or a diarylamino group; provided that when l is 3, at least one of the substituents $R_1$ to $R_7$ represents a group other than a hydrogen atom; and $Z_1$ and $Z_2$ each represents an oxygen atom, a sulfur atom or a monosubstituted nitrogen atom:

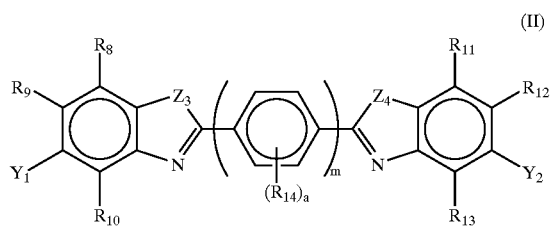

wherein each of the substituents $R_8$ to $R_{14}$ represents a hydrogen atom, a halogen atom, an alkyl group, an aryl group, an alkoxy group, an aryloxy group, an amino group, a dialkylamino group, an N-alkyl-N-arylamino group, a diarylamino group or a silyl group; m represents an integer of 1 or above; b represents an integer of from 1 to 4; $Y_1$ and $Y_2$ each represents an aryloxy group, a dialkylamino group, an N-alkyl-N-arylamino group or a diarylamino group; and $Z_3$ and Z4 each represents an oxygen atom, a sulfur atom or a monosubstituted nitrogen atom.

DETAILED DESCRIPTION OF THE INVENTION

The present compounds represented by formulae (I) and (II) respectively are described below in detail.

The substituents $R_1$ to $R_{14}$ in formulae (I) and (II) are each a hydrogen atom, a halogen atom, an alkyl group, an aryl group, an alkoxy group, an aryloxy group, a dialkylamino group, an N-alkyl-N-arylamino group or a diarylamino group. More specifically, each substituent is a hydrogen atom, a halogen atom, such as fluorine, chlorine or bromine, a substituted or unsubstituted straight-chain or branched alkyl group containing 1 to 12 carbon atoms, a substituted or unsubstituted aryl group containing 6 to 20 carbon atoms, a substituted or unsubstituted alkoxy group containing 1 to 6 carbon atoms, a substituted or unsubstituted aryloxy group containing 6 to 20 carbon atoms, a substituted or unsubstituted dialkylamino group containing 2 to 16 carbon atoms, a substituted or unsubstituted N-alkyl-N-arylamino group containing 7 to 21 carbon atoms, or a substituted or unsubstituted diarylamino group containing 12 to 36 carbon atoms. Any adjacent two of these substituents may combine with each other to form a saturated ring or an unsaturated ring (including aromatic rings).

The following are detailed description of the above-recited groups except hydrogen and halogen atoms: Examples of an alkyl group include methyl, ethyl, n-propyl, n-octyl, n-dodecyl, 2-methoxyethyl, 2-phenylmethyl, benzyl, isopropyl, isobutyl, s-butyl, t-butyl, t-amyl, t-octyl, cyclopentyl, cyclohexyl and cycloheptyl groups; those of an aryl group include phenyl, 2-, 3- or 4-methylphenyl, 4-t-butylphenyl, 4-methoxyphenyl, 4-dimethylaminophenyl, 1- or 2-naphthyl, anthryl and phenanthryl groups; those of an alkoxy groups include methoxy, ethoxy, n-propoxy, n-butoxy, n-hexyloxy, isopropoxy, isobutoxy, t-butoxy, cyclopentyloxy and cyclohexyloxy groups; those of an aryloxy group include phenoxy, 2-, 3- or 4-methylphenoxy, 4-t-butylphenoxy, 4-phenylphenoxy, 4-methoxyphenoxy, 2-cyclohexylphenoxy, 3-ethylphenoxy, 1-or 2-naphthoxy, anthryloxy and phenanthryloxy groups; those of a dialkylamino group include dimethylamino, diethylamino, dibutylamino, dioctylamino, N-methylbutylamino, bis(2-methoxyethyl)amino and bis(2-chloroethyl) amino groups; those of an N-alkyl-N-arylamino group include N-methylanilino, N-butylanilino and N-methyl-1- naphthylamino groups; and those of a diarylamino group include diphenylamino, N-(3-methylphenyl)anilino, N-(4-methylphenyl)anilino, bis(4-methylphenyl)amino, N-naphthylanilino and dinaphthylamino groups.

In cases where the groups represented by $R_1$ to $R_{14}$ have substituent groups, those which can be such substituent groups are specifically a halogen atom, an alkyl group, an aryl group, a heterocyclic group, a cyano group, a hydroxy group, a nitro group, a carboxyl group, a sulfo group, an amino group, an alkoxy group, an aryloxy group, an acylamino group, an alkylamino group, an anilino group, an ureido group, a sulfamoylamino group, an alkylthio group, an arylthio group, an alkoxycarbonylamino group, a sulfonamido group, a carbamoyl group, a sulfamoyl group, a sulfonyl group, an alkoxycarbonyl group, a heterocyclyoxy group, an azo group, an acyloxy group, a carbamoyloxy group, a silyloxy group, an aryloxycarbonylamino group, an imido group, a heterocyclylthio group, a sulfinyl group, a phosphonyl group, an aryloxycarbonyl group, an acyl group, a silyl group, an azolyl group and so on.

It is desirable that each of the substituents $R_1$ to $R_{14}$ be a hydrogen atom or an unsubstituted alkyl group, preferably a hydrogen atom or an unsubstituted alkyl group having 1 to 12 carbon atoms, particularly preferably a hydrogen atom or an unsubstituted alkyl group having 1 to 8 carbon atoms.

$X_1$ and $X_2$ in formula (I) are each an alkoxy group, an aryloxy group, a dialkylamino group, an N-alkyl-N-arylamino group or a diarylamino group. These groups have the same meanings as in the above description of $R_1$ to $R_{14}$, respectively.

Preferably, $X_1$ and $X_2$ are each an alkoxy group, a dialkylamino group or a diarylamino group.

$Y_1$ and $Y_2$ in formula (II) are each an aryloxy group, a dialkylamino group, an N-alkyl-N-arylamino group or a diarylamino group. These groups have the same meanings as in the above description of $R_1$ to $R_{14}$ respectively.

Preferably, $Y_1$ and $Y_2$ are each a dialkylamino group or a diarylamino group.

$Z_1$, $Z_2$, $Z_3$ and $Z_4$ in formulae (I) and (II) areeach anoxygen atom, a sulfur atom or a monosubstituted nitrogen atom. The term "monosubstituted nitrogen atom" as used herein refers to the nitrogen atom substituted by an alkyl or aryl group. The alkyl or aryl group on the nitrogen atom has the same meaning as in the above description of $R_1$ to $R_{14}$. The atom preferred as $Z_1$ to $Z_4$ is an oxygen atom.

l in formula (I) is an integer of 1 or above, preferably an integer of from 1 to 4. Of these integers, 2 is particularly preferred as l.

When l is 3, at least one of the substituents $R_1$ to $R_7$ does not represent a hydrogen atom. In this case, it is desirable for such a substituent to be an alkyl group or a dialkylamino group.

m in formula (II) is an integer of 1 or above, preferably an integer of from 1 to 4. Of these integers, 2 is particularly preferred as m.

a and b in formula (I) and (II) respectively are each an integer of from 1 to 4, preferably 1 or 2.

Further, rings may be formed by combining $R_1$, $R_2$, $R_4$ or $R_5$ with $X_1$ or $X_2$ and combining $R_9$, $R_{10}$, $R_{12}$ or $R_{13}$ with $Y_1$ or $Y_2$. The suitable number of member atoms of such rings is from 5 to 7.

Specific examples of compounds represented by the present formulae (I) and (II) respectively are illustrated below, but it should be understood that these examples are not to be construed as limiting the scope of the invention in any way.

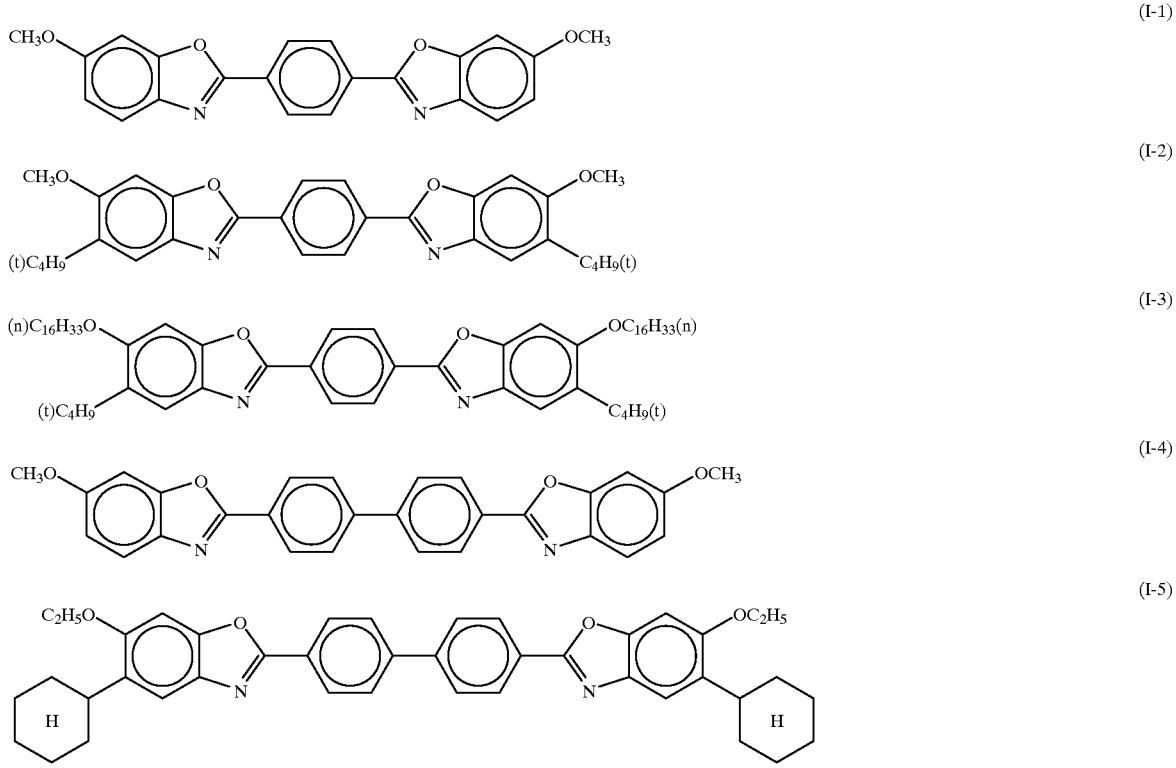

-continued
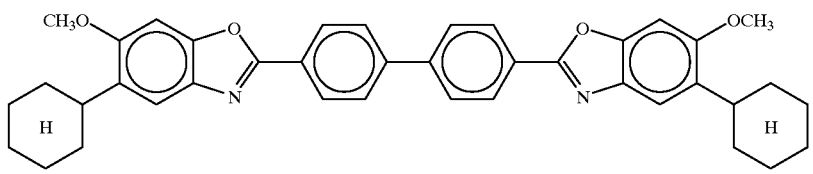
(I-6)
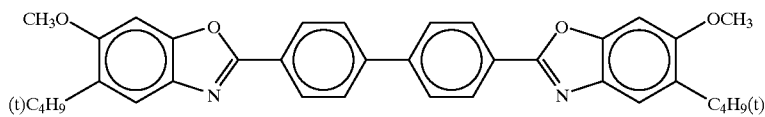
(I-7)
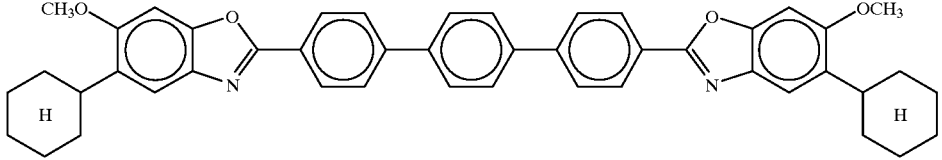
(I-8)
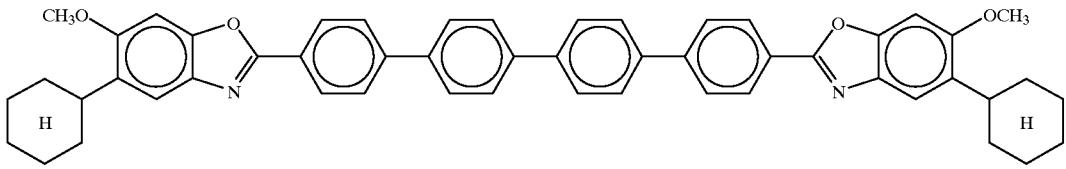
(I-9)
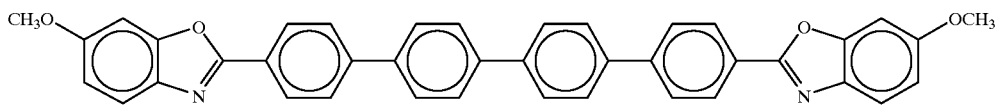
(I-10)
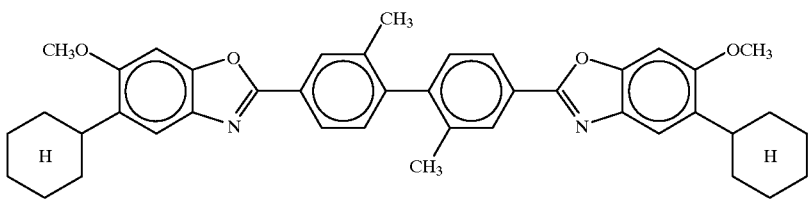
(I-11)
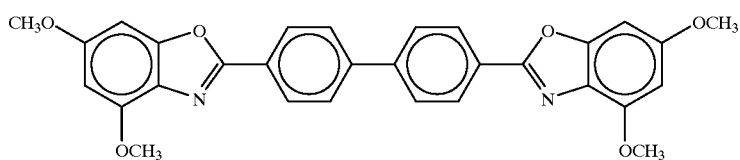
(I-12)
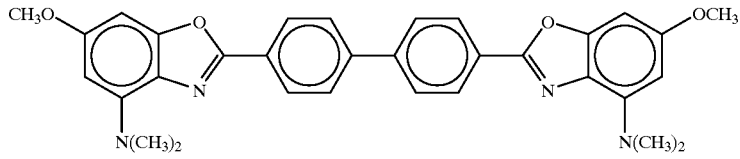
(I-13)
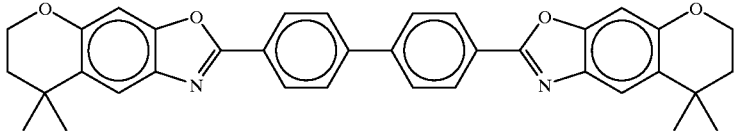
(I-14)

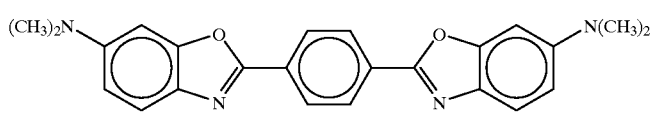
(I-15)
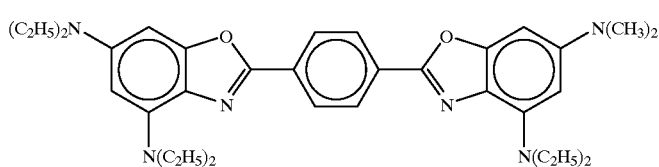
(I-16)
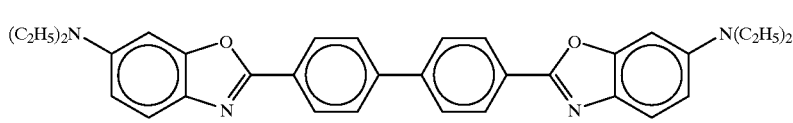
(I-17)
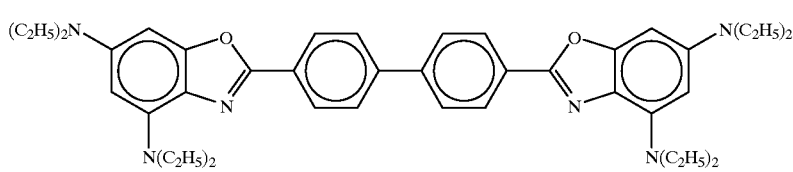
(I-18)
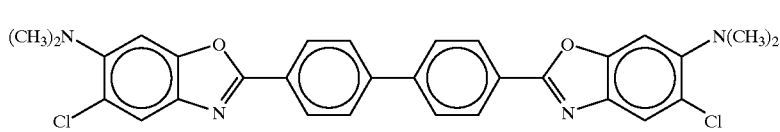
(I-19)
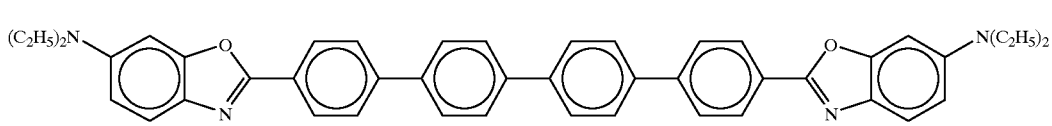
(I-20)
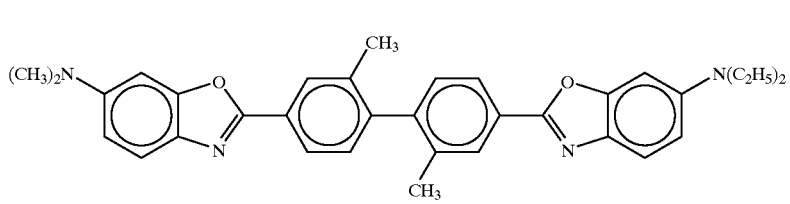
(I-21)
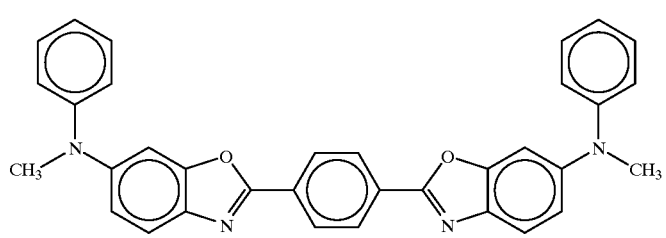
(I-22)
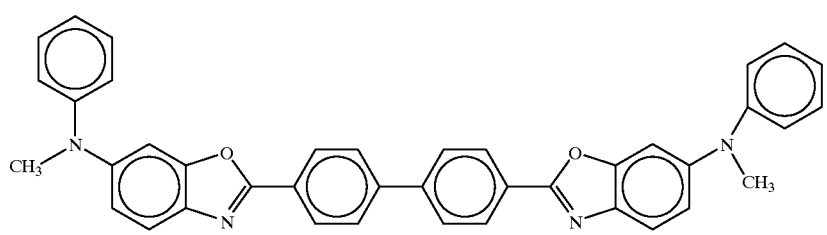
(I-23)

(I-24)
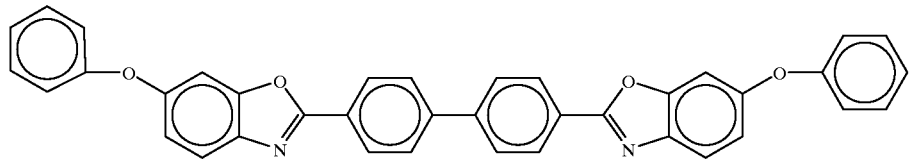
(I-25)
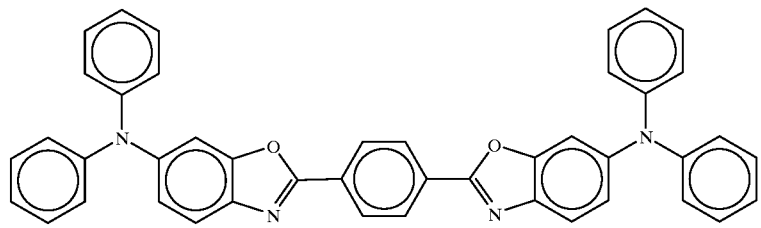
(I-26)
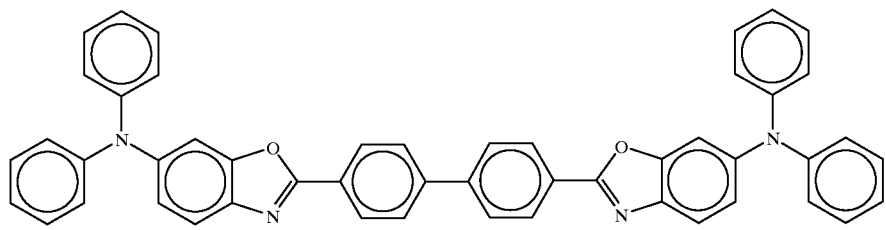
(I-27)
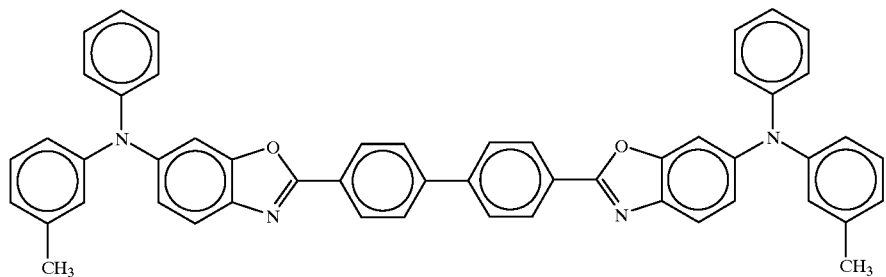
(I-28)
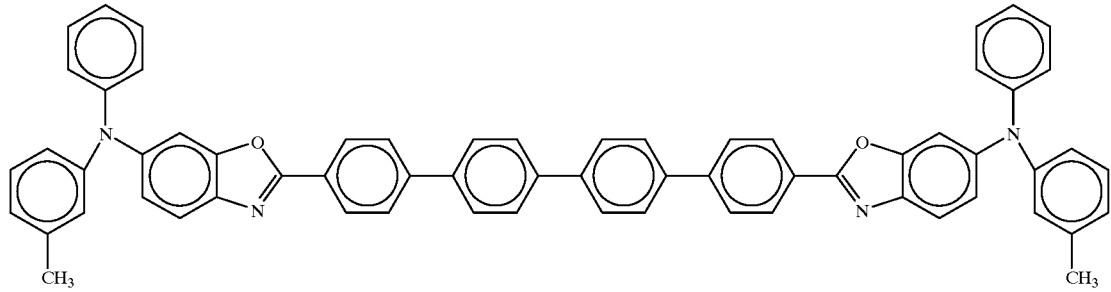
(I-29)
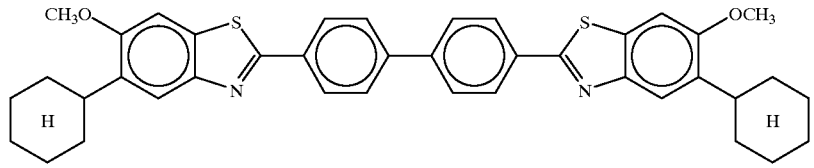

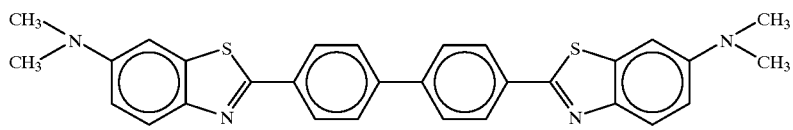
(I-30)
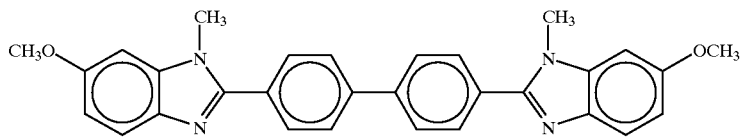
(I-31)
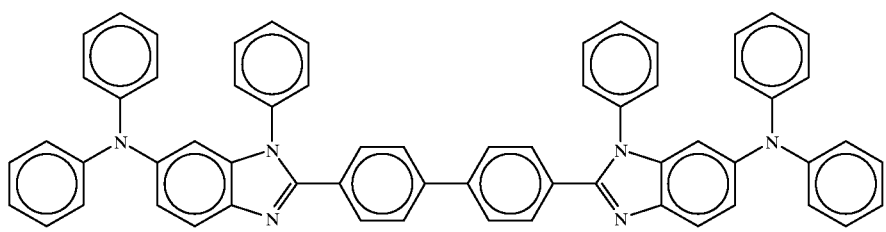
(I-32)
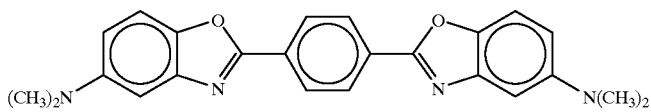
(II-1)
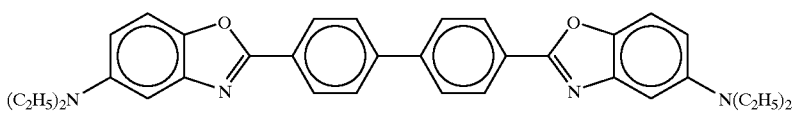
(II-2)
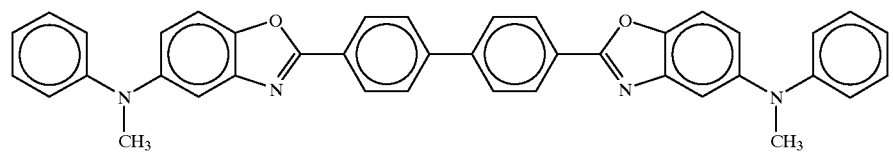
(II-3)
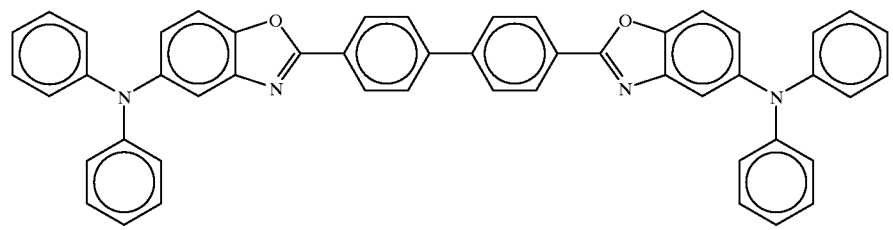
(II-4)
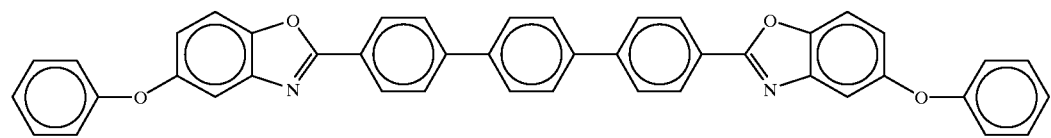
(II-5)
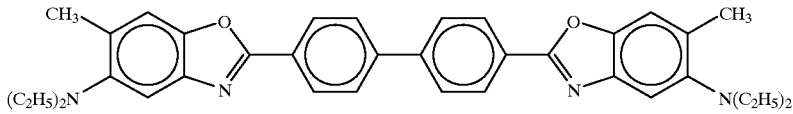
(II-6)

-continued
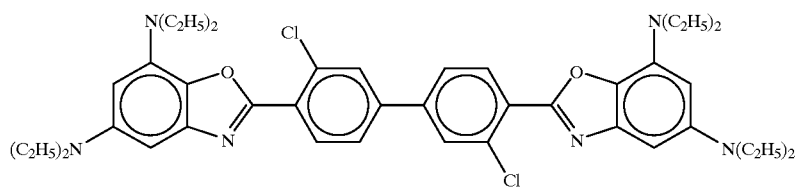
(II-7)
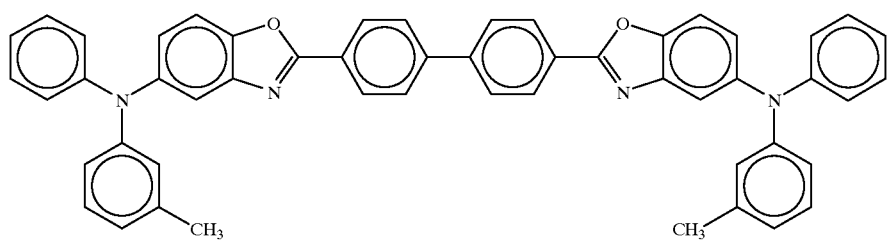
(II-8)
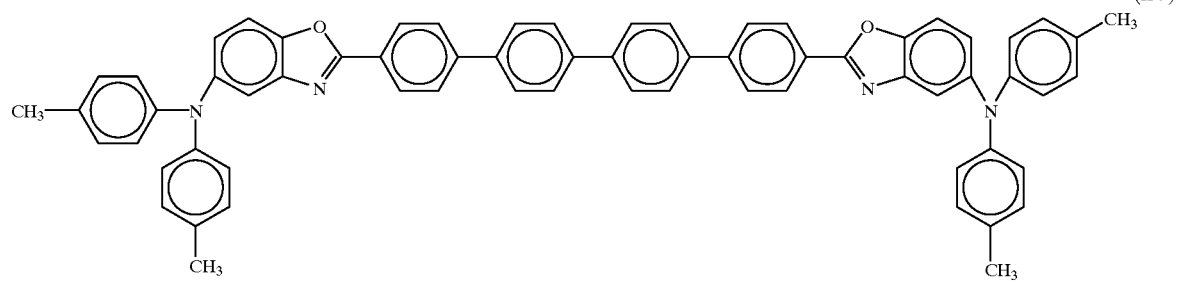
(II-9)
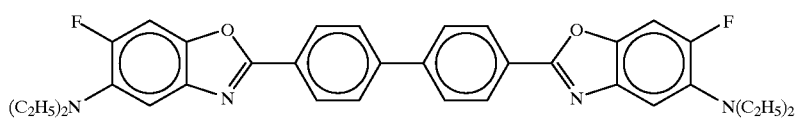
(II-10)
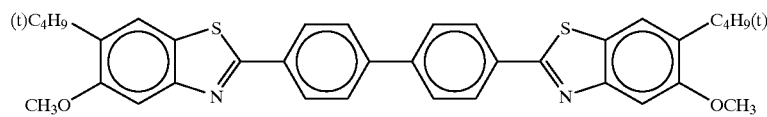
(II-11)
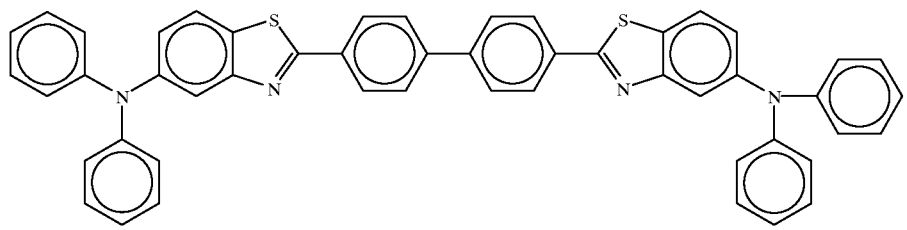
(II-12)
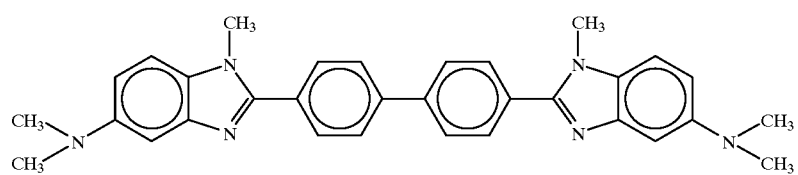
(II-13)

(II-14)

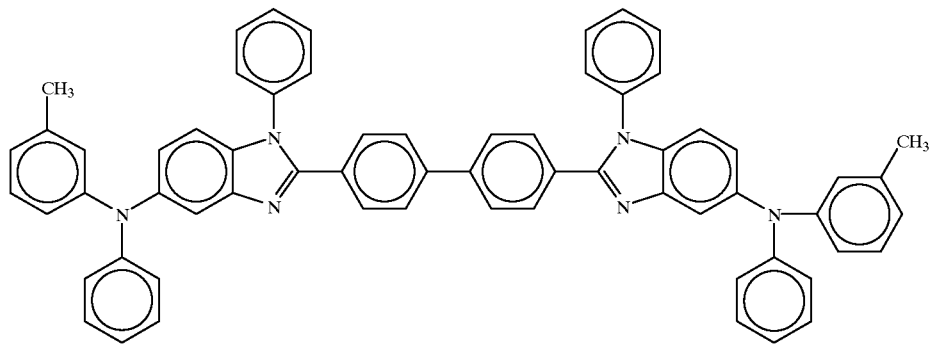

To take compounds of formula (I) as examples, the synthetic methods of the present compounds are illustrated below.

The following <Scheme 1> is a typical synthetic method which can be adopted when l and m are each 1 or 2, and the following <Scheme 2> is representative of the synthetic method utilizable in the cases where l and m are each at least 2. Especially when the compounds are asymmetric besides having l of at least 2 and m of at least 2 in formula (I), the following <Scheme 3> can be effectively adopted.

<Scheme 1>

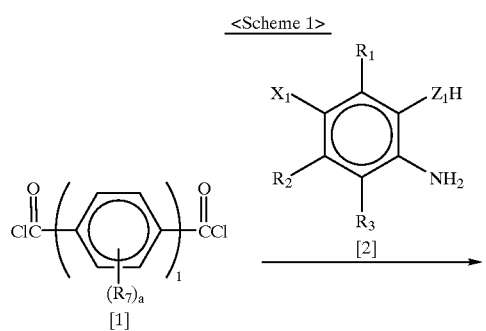

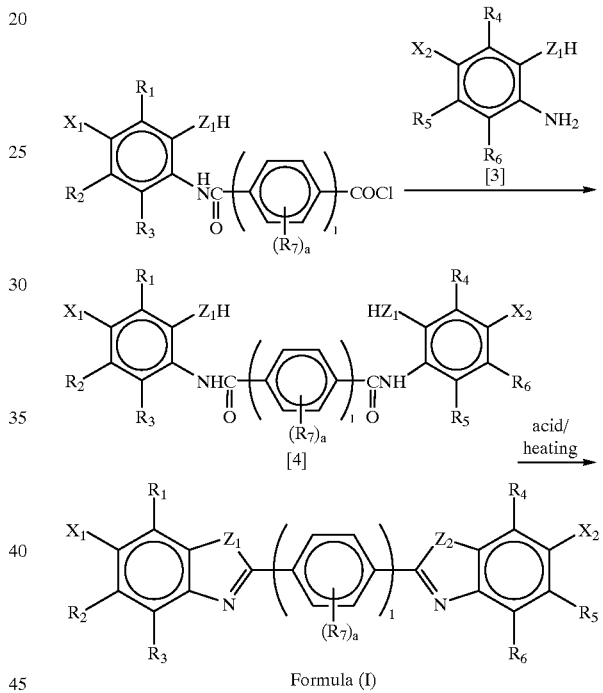

In the above formulae, $R_1$ to $R_6$, $X_1$, $X_2$, $Z_1$ and $Z_2$ have the same meanings as defined hereinbefore, respectively.

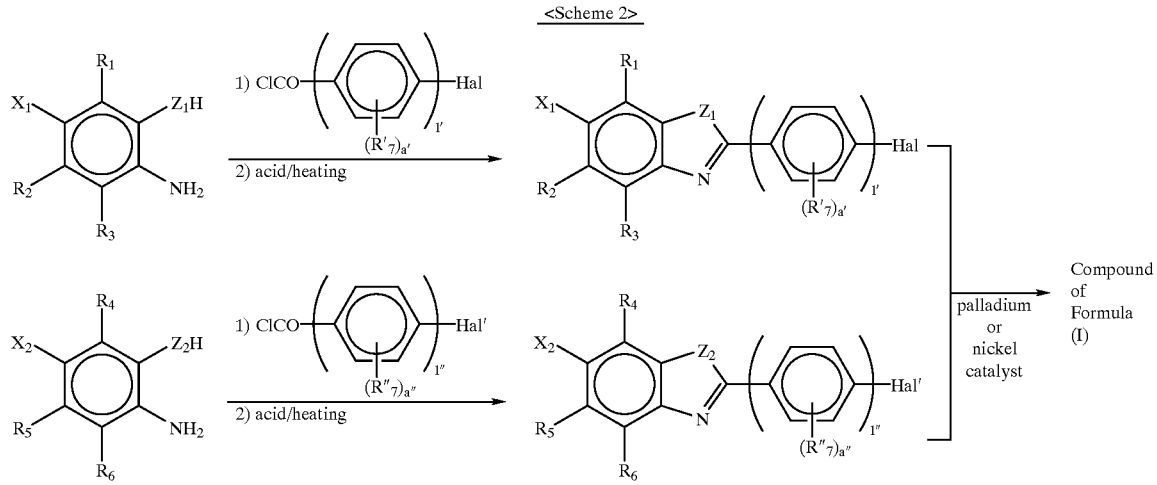

In the above formulae, $R_1$ to $R_6$, $X_1$, $X_2$, $Z_1$ and $Z_2$ have the same meanings as defined hereinbefore respectively, $R_7'$, and $R_7''$ each have the same meaning as $R_7$ defined hereinbefore, a' and a'' are each the same integer as "a" defined hereinbefore, l' and l'' are integers the sum of which is 1, and Hal and Hal' are each a chlorine, bromine or iodine atom.

In the case of formula (II) also, the same synthetic methods as illustrated above can be utilized.

The present compounds synthesized in accordance with the scheme as illustrated above are purified by undergoing

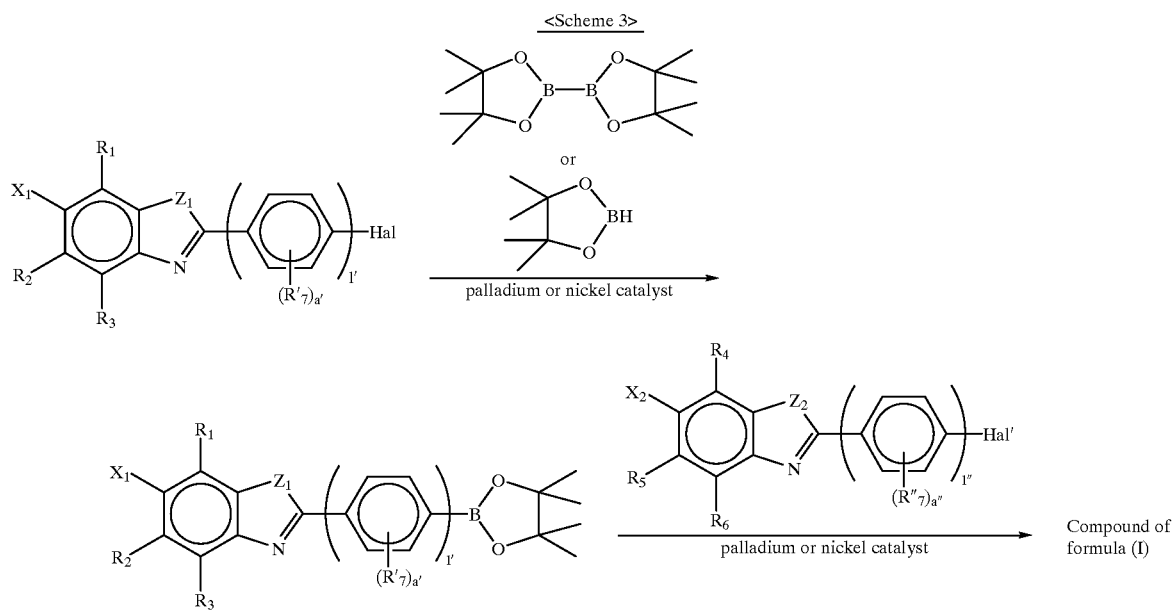

In the above formulae, $R_1$ to $R_6$, $X_1$, $X_2$, $Z_1$ and $Z_2$ have the same meanings as defined hereinbefore respectively, $R_7'$ and $R_7''$ each have the same meaning as $R_7$ defined hereinbefore, a' and a'' are each the same integer as "a" defined hereinbefore, l' and l'' are integers the sum of which is 1, and Hal and Hal' are each a chlorine, bromine or iodine atom.

silica gel column chromatography and recrystallization, and further sublimation if needed.

The present invention will now be illustrated in more detail by reference to the following examples. However, the invention should not be construed as being limited to the following examples.

EXAMPLE 1

Synthesis of Exemplified Compound (I-3)

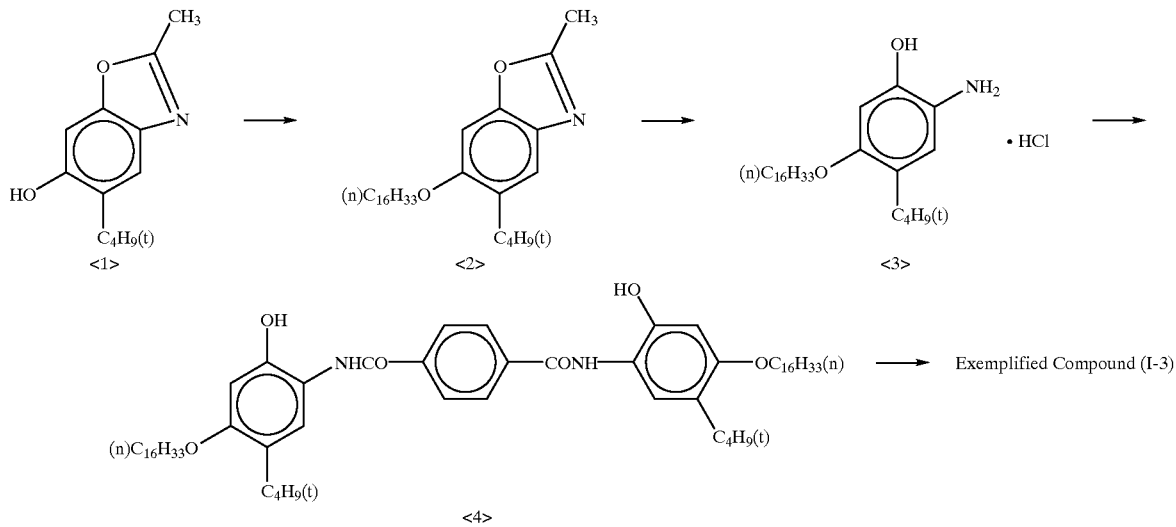

Compound <3> illustrated above was synthesized according to the method described in JP-A-56-100771.

More specifically, 101 g (0.52 mol) of Compound <1> was dissolved in 330 ml of dimethylformamide (DMF), and thereinto 40 g (1.0 mol) of sodium hydroxide was put with stirring at room temperature. Thereto, 195 g (0.64 mol) of cetyl bromide was added, and heated up to about 80° C. After a 5-hour lapse, the resulting mixture was extracted with ethyl acetate, post-treated, and then concentrated under reduced pressure to yield crude crystals of Compound <2>. To these crystals, 700 ml of methyl cellosolve and 393 ml of concentrated hydrochloric acid were added, and heated under reflux for about 8 hours. Upon cooling the reaction solution to room temperature, crystals separated out. These crystals were dispersed into acetonitrile (600 ml) with stirring, and filtered off with suction. Thus, 218 g (95% yield) of nearly pure Compound <3> was obtained.

The NMP (which stands for N-methylpyrrolidone) solution (300 ml) containing 15 g (73.9 mmol) of 1,4-benzenedicarboxylic acid chloride was admixed with 65.4 g (148 mmol) of Compound <3>, and stirred at room temperature. After the stirring was continued for 30 minutes, the reaction solution was allowed to stand for one night. As a result, crystals of Compound <4> were deposited. These crystals were admixed with methanol, and filtered off.

The thus obtained yellow crystals (Compound <4>) were placed in a flask, and thereto were added 200 ml of chlorobenzene, 300 ml of NMP and 7.0 g (37 mmol) of p-toluenesulfonic acid hydrate. Then, the flask was heated so that the external temperature thereof was maintained at about 240° C. The heating was continued for about 4 hours while removing water and some quantity of chlorobenzene, and then the contents of the flask was allowed to stand for one night at room temperature, thereby depositing crystals. These crystals was admixed with methanol, and sucked off to yield white crystals. These crystals were recrystallized from ethyl acetate to give 56.4 g (84.3% yield) of the exemplified Compound (I-3), mp.(melting point): 88–91° C.

EXAMPLE 2

Synthesis of Exemplified Compound (I-4)

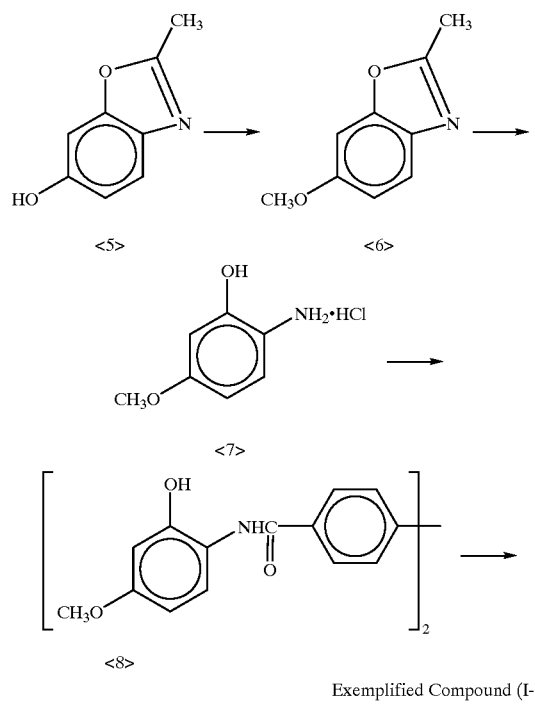

Exemplified Compound (I-4)

The above Compound <5> in an amount of 5.0 g (33.5 mmol) was dissolved in 100 ml of dimethylformamide (DMF), and thereto 5.0 g (40.2 mmol) of 90% potassium t-butoxide was added at room temperature. After 30 minutes' stirring, 5.1 g (40.4 mmol) of dimethyl sulfate was added thereto. The resulting mixture was stirred for 1 hour, extracted with ethyl acetate, post-treated, and then concentrated under reduced pressure to yield crude crystals of Compound <6>. These crude crystals were dissolved in 100 ml of methanol, admixed with 10 ml of concentrated hydrochloric acid, and then heated under reflux for about 8 hours. The reaction solution obtained was concentrated to dryness. Thus, crude crystals of Compound <7> were obtained. These crystals were dispersed in ethyl acetate, and filtered off with suction to give 4.4 g (75% yield) of nearly pure Compound <7>.

A solution containing 4.0 g (22.8 mmol) of Compound <7> and 29 g (10.4 mmol) of 4,4'-biphenyldicarbonyl chloride in 50 ml of acetonitrile was stirred, and thereto 4.6 ml (33.2 mmol) of triethylamine was added dropwise. After the conclusion of the dropwise addition, the solution was heated under reflux for about 2 hours, cooled to room temperature, and then admixed with about 50 ml of water to fully deposit crystals. These crystals were filtered off with suction, washed with methanol, and then dried to give 8.3 g (75% yield) of light yellow crystals of Compound <8>.

P-toluenesulfonic acid hydrate in an amount of 9.4 g (49.5 mmol) was added to a toluene solution (100 ml) containing 8.0 g (16.5 mmol) of Compound <8>, and heated under reflux for about 8 hours while the water removal was carried out with a Dean-Stark water removing apparatus. Then, the reaction mixture was cooled to room temperature. The crystals thus deposited were filtered off with suction, washed successively with saturated solution of sodium carbonate, distilled water and tetrahydrofuran, and then dried to give 4.1 g (55% yield) of the exemplified Compound (I-4) as light yellow crystals, mp.: higher than 300° C.

EXAMPLE 3

Synthesis of Exemplified Compound (I-5)

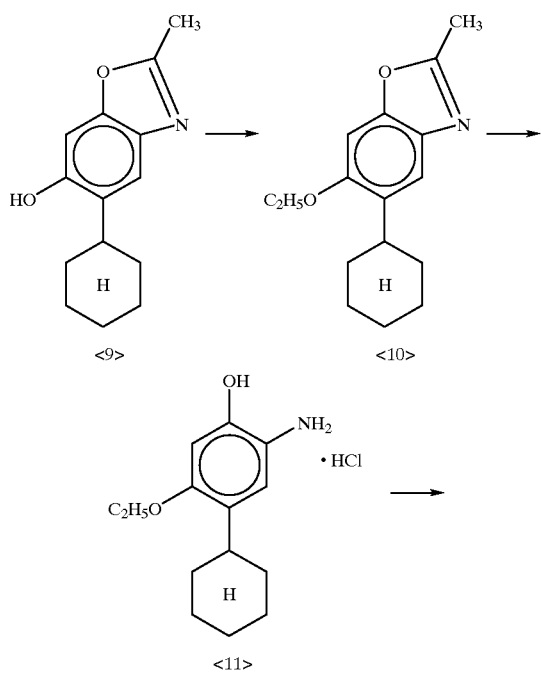

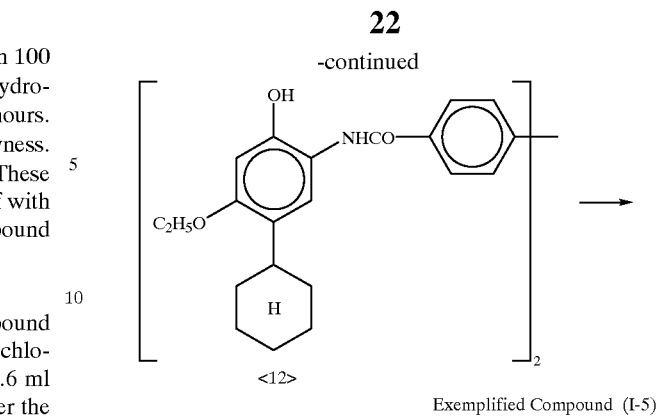

Exemplified Compound (I-5)

The above Compound <9> in an amount of 10 g (43.2 mmol) was dissolved in 100 ml of dimethylacetamide (DMAC). To this solution, 6.5 g (51.8 mmol) of potassium t-butoxide was added, and stirred for about 30 minutes at room temperature. Thereto, 8.1 g (51.8 ml) of iodoethane was further added dropwise, and stirred for a while. Whether or not the Compound <9> was present in the resulting solution was checked by TLC. After the disappearance of Compound <9> was confirmed, the reaction solution was admixed with water, and extracted twice with ethyl acetate. The extract was washed with water and saturated brine, dried over magnesium sulfate, filtered, and then concentrated under reduced pressure to give Compound <10> contaminated with some quantity of DMAC. To this material, 100 ml of methanol and 15 ml (0.18 mol) of concentrated hydrochloric acid were added, and heated under reflux for about 5 hours. The reaction solution thus obtained was concentrated under reduced pressure as it was, and the residue was admixed with toluene and methanol. The admixture was concentrated again under reduced pressure. To the crystals thus obtained, ethyl acetate was added, and stirred. Then, the crystals were filtered off with suction, and dried to give 8.9 g (76% yield) of Compound <10> as light yellow crystals.

An acetonitrile solution (100 ml) containing 2.3 g (8.4 mmol) of 4,4'-biphenyldicarbonyl chloride was stirred at room temperature, and thereto was added 5.0 g (18.4 mmol) of 2-amino-4-cyclohexyl-5-ethoxyphenol hydrochloride (Compound <11>). Further, 3.7 ml (26.9 mmol) of triethylamine was added dropwise thereto, and heated under reflux for about 2 hours. The reaction solution was cooled to room temperature, and then water was added thereto. Light brown crystals thus deposited were filtered off with suction, and washed thoroughly with methanol. The thus obtained crystals were Compound <12> as amide body. The yield thereof was 4.3 g (75.7%).

A toluene solution (100 ml) containing 4.0 g (5.9 mmol) of the amide body <12> and 3.3 g (17.3 mmol) of paratoluenesulfonic acid hydrate was heated under reflux for about 16 hours while the removal of water was carried out with a Dean-Stark water removing apparatus. Thereafter, the reaction solution was cooled to room temperature. The crystals thus deposited were filtered off with suction, and washed with toluene to give yellow crystals. These crystals were placed in a beaker, and a saturated aqueous solution of sodium hydrogen carbonate was added thereto and stirred. The resulting matter was filtered again with suction, washed with water, and then dried to give 2.1 g (55% yield) of the exemplified Compound (I-5) as light yellow crystals tinged with yellowish green, mp. 259–260° C. (recrystallized from tetrahydrofuran)

EXAMPLE 4

Synthesis of Exemplified Compound (I-6)

An acetonitrile solution (100 ml) containing 2.3 g (8.4 mmol) of 4,4'-biphenyldicarbonyl chloride was stirred at room temperature, and thereto was added 5.0 g (19.4 mmol) of 2-amino-4-cyclohexyl-5-methoxyphenol hydrochloride. Further, 3.7 ml (26.9 mmol) of triethylamine was added dropwise thereto, and heated under reflux for about 2 hours. The reaction solution was cooled to room temperature, and then water was added thereto. Light brown crystals thus deposited were filtered off with suction, and washed thoroughly with methanol. Thus, the diamide body was obtained as crystals, and the yield thereof was 4.3 g (78%).

A toluene solution (100 ml) containing 4.0 g (6.2 mmol) of the diamide body and 3.3 g (17.3 mmol) of p-toluenesulfonic acid hydrate was heated under reflux for about 16 hours while the removal of water was carried out with a Dean-Stark apparatus. Thereafter, the reaction solution was cooled to room temperature. The crystals thus deposited were filtered off with suction, and washed with toluene to give yellow crystals. These crystals were placed in a beaker, and a saturated aqueous solution of sodium hydrogen carbonate was added thereto and stirred. The resulting matter was filtered again with suction, washed with water, and then dried to give 2.3 g (60% yield) of the exemplified Compound (I-6) as light yellow crystals, mp.: 283–285° C. (recrystallized from tetrahydrofuran).

EXAMPLE 5

Synthesis of Exemlified Compound (I-9)

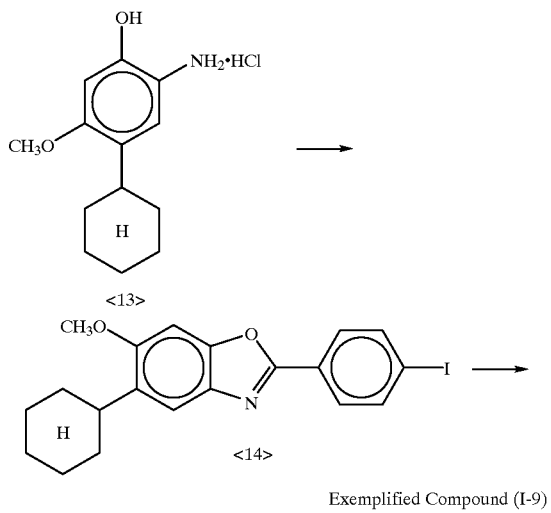

Exemplified Compound (I-9)

4-Iodobenzoic acid in an amount of 17.3 g (70 mmol) was dissolved in 100 ml of NMP (N-methylpyrrolidone), and cooled to about 10° C. with stirring by means of ice-cold water. Thereto, 5.9 ml (81 mmol) of thionyl chloride was added dropwise, and then stirred for about 2 hours. To this reaction solution, Compound <13> illustrated above was added in an amount of 15.0 g (58 mmol), and stirred for about 2 hours. Further, the reaction solution was admixed with water, and extracted twice with chloroform. The combined extracts was washed successively with a water solution of sodium hydroxide (pH=about 8) and saturated brine, dried over anhydrous magnesium sulfate, filtered, and then concentrated. To the concentrate in which NMP was contained, 100 ml of toluene and 2.2 g (12 mmol) of p-toluenesulfonic acid hydrate were added, and the dehydration was carried out while the toluene was removed with a Dean-Stark apparatus. After most of the toluene was removed therefrom, the reaction mixture was admixed with 100 ml of chlorobenzene, and heated under reflux for about 15 hours. The reaction solution thus obtained was extracted with water and chloroform, and thereby a crystalline compound was obtained. This compound was admixed with methanol, and filtered off to give 21.6 g (86.1% yield) of light yellowish brown Compound <14>.

The Compound <14> in an amount of 5 g (11.5 mmol), 1.4 g (5.8 mmol) of 4,4'-biphenyldiborate and 0.1 g (0.087 mmol) of tetrakistriphenylphosphine palladium were placed in a flask, and thereto 11.5 ml (23 mmol) of a 2 M aqueous solution of sodium carbonate and 80 ml of toluene were added. The resulting matter was heated under reflux in a stream of nitrogen. Therein, however, the reactant compounds did not mix well, so that 90 ml of DMF and 30 ml of water were further added thereto and heated under reflux for about 20 hours. The resulting reaction solution was cooled to room temperature, and admixed with water to deposit crystals. These crystals were filtered off, and washed with methanol. The crystals obtained were placed in a Soxhlet extractor and extracted with chloroform to give 2.7 g (61.4% yield) of the exemplified Compound (I-9) as pure crystals, mp.: 275–276° C.

EXAMPLE 6

Synthesis of Exemplified Compound (I-17)

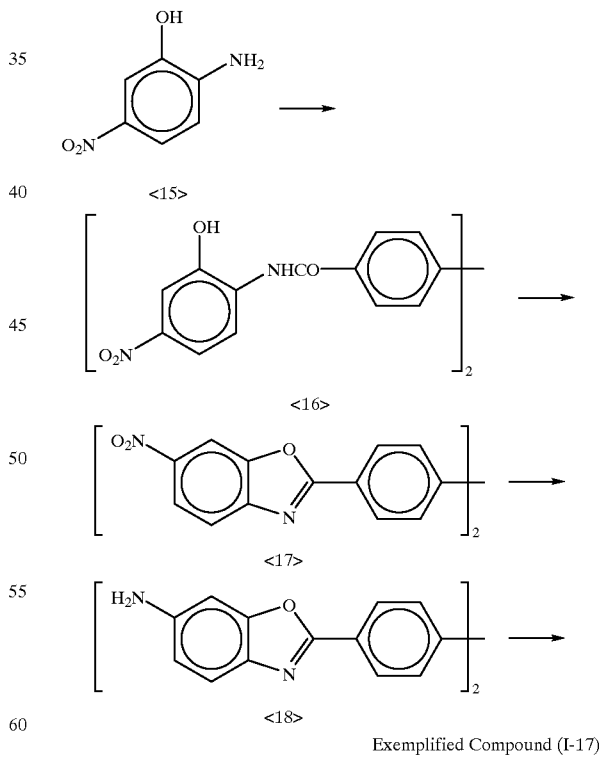

Exemplified Compound (I-17)

To an acetonitrile solution (100 ml) containing 12.1 g (78.8 mmol) of 2-amino-5-nitrophenol (Compound <15>), 10.0 g (35.8 mmol) of 4,4'-biphenyldicarboxylic acid chloride was added, and stirred. Thereto, 8.0 g (78.8 mmol) of triethylamine was added dropwise, and then stirred for about 2 hours. The crystals thus deposited were filtered off, washed with acetonitrile, and then dried to give 17.0 g (92.3% yield) of Compound <16> as yellow crystals.

To 15.0 g of Compound <16> were added 200 ml of DMI (which stands for 1,3-dimethyl-2-imidazolidinone) and 100 ml of toluene. Further, 16.6 g (87.5 mmol) of p-toluenesulfonic acid hydrate was added thereto, and heated under reflux for about 15 hours. During the heating under reflux, water was removed with a Dean-Stark apparatus. Then, the reaction solution was cooled to room temperature, and thereby crystals were deposited. These crystals were filtered off, and dried to give 12.1 g (76.5% yield) of Compound <17> as yellow powdery crystals.

Reduced iron in an amount of 5.8 g (105 mmol) was put in 100 ml of isopropanol, and thereto 0.6 g (10.5 mmol) of ammonium chloride and 30 ml of water were added. The resulting mixture was heated under reflux for about 30 minutes. The heating under reflux was intermitted, and 5.0 g (10.5 mmol) of Compound <17> was added to the reaction solution, and further 300 ml of DMF (N,N-dimethylformamide) was added thereto. The resulting solution was heated under reflux for about 6 hours, and then cooled to about 50° C. The insoluble matter therein was filtered out with Celite. The filtrate was concentrated with an evaporator to remove the isopropanol and the water. To the residue obtained, wherein Compound <18> was contained, 50 g (320 mmol) of iodoethane and 20 g (145 mmol) of potassium carbonate were added, and the reaction was run at 65–75° C. for about 20 hours. The reaction solution obtained was admixed with chloroform and water, filtered with Celite, and then subjected to an extraction procedure. The extract obtained was dried over anhydrous magnesium sulfate, filtered, and then concentrated to give a crystalline compound. This crystalline compound was put in methanol, stirred and then filtered off with suction. Thus, 3.8 g of yellow crystals containing the exemplified Compound (I-17) as a main component was obtained. These crystals were purified by silica gel column chromatography (eluant: chloroform), and subsequently recrystallized from tetrahydrofuran. Thus, 2.0 g (35.9% yield) of the exemplified Compound (I-17) was obtained in a pure form. mp.: 232–233° C.

EXAMPLE 7

Synthesis of Exemplified Compound (I-27)

In the same manner as in Example 4, 2.1 g (65% yield) of the exemplified Compound (I-27) was obtained using 3.3 g (10 mmol) of 2-amino-5-(N-phenyl-N-m-tolylamino)phenol hydrochloride and 1.2 g (4.3 mmol) of 4,4'-biphenyldicarbonyl chloride. mp.: 250–253° C.

EXAMPLE 8

Synthesis of Exemplified Compound (II-2)

The exemplified Compound (II-2) was obtained in an amount of 3.5 g (total yield of 18%) in almost the same manner as in Example 6, except that 2-amino-4-nitrophenol was used in place of 2-amino-5-nitrophenol (Compound <15>). mp.: 251–252° C.

EXAMPLE 9

Synthesis of Exemplified Compound (II-4)

In the same manner as in Example 4, the exemplified Compound (II-4) was obtained in an amount of 2.2 g (total yield of 70%) by the use of 3.1 g (10.0 mmol) of 2-amino-4-diphenylaminophenol hydrochloride and 1.2 g (4.3 mmol) of 4,4'-diphenyldicarbonyl chloride. mp.: 265–267° C.

EXAMPLE 10

Synthesis of Exemplified Compound (II-5)

In the same manner as in Example 4, the exemplified Compound (II-5) was obtained in an amount of 2.0 g (80% yield) by the use of 2.4 g (10.0 mmol) of 2-amino-4-phenoxyphenol hydrochloride and 1.2 g (4.3 mmol) of 4,4'-diphenyldicarbonyl chloride. mp.: 280–283° C.

ADVANTAGES OF THE INVENTION

Bisbenzazole compounds according to the present invention have excellent vacuum deposition suitability and, when used in organic electroluminescence elements, they function as a blue light emission electron transfer material having high stability and excellent luminance characteristics. Besides acting as a blue light emitting material, the present bisbenzazole compounds function effectively as a host material in the case of emitting green or red light by the use of a doping agent.

Thus, the discovery of the present bisbenzazole compounds can make it easy to design full-color organic electroluminescence elements.

What is claimed is:

1. A bisbenzazole compound represented by the following formula (I) or (II):

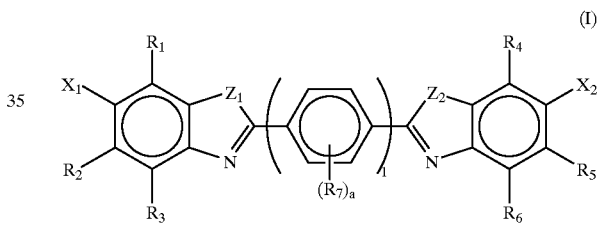

wherein each of the substituents $R_1$ to $R_7$ represents a hydrogen atom, a halogen atom, an alkyl group, an aryl group, an alkoxy group, an aryloxy group, an amino group, a dialkylamino group, an N-alkyl-N-arylamino group, a diarylamino group or a silyl group; l represents an integer of 1 or above; a represents an integer of from 1 to 4; $X_1$ and $X_2$ each represents an alkoxy group, an aryloxy group, a dialkylamino group, an N-alkyl-N-arylamino group or a diarylamino group, provided that $X_1$ and $X_2$ are not both a diethylamino group; provided that when l is 3, at least one of the substituents $R_1$ to $R_7$ represents a group other than a hydrogen atom; and $Z_1$ and $Z_2$ each represents an oxygen atom, a sulfur atom or a monosubstituted nitrogen atom:

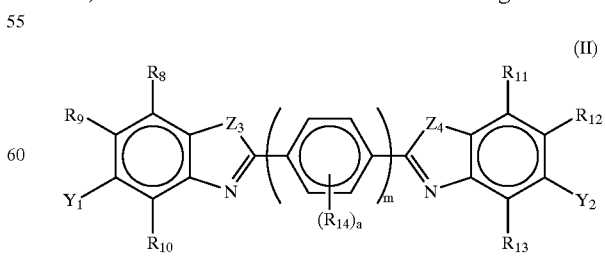

wherein each of the substituents $R_8$ to $R_{14}$ represents a hydrogen atom, a halogen atom, an alkyl group, an aryl group, an alkoxy group, an aryloxy group, an amino group, a dialkylamino group, an N-alkyl-N-arylamino group, a diarylamino group or a silyl group; m represents an integer of 1 or above; b represents an integer of from 1 to 4; $Y_1$, and $Y_2$ each represents an aryloxy group, a dialkylamino group, an N-alkyl-N-arylamino group or a diarylamino group; and $Z_3$ and $Z_4$ each represents an oxygen atom, a sulfur atom or a monosubstituted nitrogen atom.

2. The bisbenzazole compound according to claim 1, wherein $R_1$ to $R_{14}$ are each a hydrogen atom or an unsubstituted alkyl group having 1 to 12 carbon atoms.

3. The bisbenzazole compound according to claim 1, wherein $R_1$ to $R_{14}$ are each a hydrogen atom or an unsubstituted alkyl group having 1 to 8 carbon atoms.

4. The bisbenzazole compound according to claim 1, where $X_1$ and $X_2$ are each an alkoxy group, a N-alkyl-N-arylamino group or a diarylamino group.

5. The bisbenzazole compound according to claim 1, wherein $Y_1$ and $Y_2$ are each a dialkylamino group or a diarylamino group.

6. The bisbenzazole compound according to claim 1, wherein $Z_1$, $Z_2$, $Z_3$ and $Z_4$ are each an oxygen atom.

7. The bisbenzazole compound according to claim 1, wherein l in formula (I) is an integer of from 1 to 4.

8. The bisbenzazole compound according to claim 7, wherein l is 2.

9. The bisbenzazole compound according to claim 1, wherein m in formula (II) is an integer of from 1 to 4.

10. The bisbenzazole compound according to claim 9, wherein m is 2.

11. The bisbenzazole compound according to claim 1, wherein a is 1 or 2.

12. The bisbenzazole compound according to claim 1, wherein b is 1 or 2.

13. A bisbenzazole compound represented by the following formula (I) or (II):

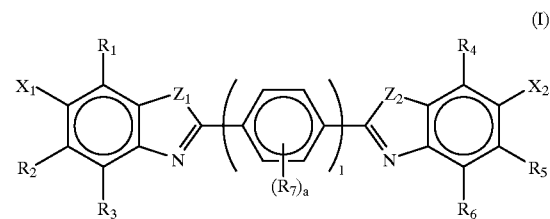

wherein each of the substituents $R_1$ to $R_7$ represents a hydrogen atom or an unsubstituted alkyl group; l represents an integer of from 1 to 4; a represents an integer of from 1 to 2; $X_1$ and $X_2$ each represents an alkoxy group, a N-alkyl-N-arylamino group or a diarylamino group; provided that when l is 3, at least one of the substituents $R_1$ to $R_7$ represents a group other than a hydrogen atom; and $Z_1$ and $Z_2$ each represents an oxygen atom:

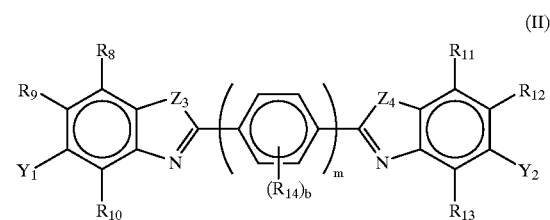

wherein each of the substituents $R_8$ to $R_{14}$ represents a hydrogen atom or an unsubstituted alkyl group; m represents an integer of from 1 to 4; b represents an integer of from 1 to 2; $Y_1$ and $Y_2$ each represents a N-alkyl-N-arylamino group or a diarylamino group; and $Z_3$ and $Z_4$ each represents an oxygen atom.

* * * * *